US012440197B2

(12) United States Patent
Srikanth et al.

(10) Patent No.: US 12,440,197 B2
(45) Date of Patent: Oct. 14, 2025

(54) LIQUID ADHESIVE DISPENSER DEVICE

(71) Applicant: Becton, Dickinson and Company, Franklin Lakes, NJ (US)

(72) Inventors: Akshay Srikanth, Bengaluru (IN); Ruben Rodrigues, Bangalore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 333 days.

(21) Appl. No.: 18/094,878

(22) Filed: Jan. 9, 2023

(65) Prior Publication Data

US 2024/0225627 A1 Jul. 11, 2024

(51) Int. Cl.
*A61B 17/00* (2006.01)
*A61M 35/00* (2006.01)

(52) U.S. Cl.
CPC ..... *A61B 17/00491* (2013.01); *A61M 35/003* (2013.01)

(58) Field of Classification Search
CPC ... A61B 17/00491; A61B 2017/00513; A61M 35/003; A45D 34/041
See application file for complete search history.

(56) References Cited

U.S. PATENT DOCUMENTS

| | | | |
|---|---|---|---|
| 8,550,737 B2 | 10/2013 | Ruiz, Sr. et al. | |
| 9,066,711 B2 | 6/2015 | Ruiz, Sr. et al. | |
| 10,722,688 B2 | 7/2020 | Zhang et al. | |
| 2002/0176732 A1 | 11/2002 | Quintero et al. | |
| 2002/0192011 A1 | 12/2002 | Bobo et al. | |
| 2003/0050613 A1* | 3/2003 | Hammerslag | A61B 17/085 604/290 |
| 2008/0107475 A1* | 5/2008 | Wojcik | A61M 35/003 401/219 |
| 2016/0015373 A1 | 1/2016 | Russo et al. | |
| 2018/0222618 A1* | 8/2018 | Zhang | B65D 65/38 |
| 2021/0196254 A1 | 7/2021 | Russo | |
| 2022/0016661 A1* | 1/2022 | Tobin | B05C 1/00 |

* cited by examiner

*Primary Examiner* — Tuan V Nguyen
(74) *Attorney, Agent, or Firm* — SERVILLA WHITNEY LLC

(57) ABSTRACT

Provided herein is a liquid adhesive dispenser device, including a housing having a first housing part having a proximal end, a distal end, a first port at the distal end, and a sidewall therebetween defining a first chamber configured to hold a liquid adhesive, a second housing part, having a proximal end, a distal end, a second port at the distal end, and a sidewall therebetween defining a second chamber configured to receive a liquid adhesive, and a ball applicator arranged adjacent the second port, wherein the first housing part has a distally-extending protrusion arranged to seal the first port, wherein the second housing part has a first seat arranged adjacent the proximal end thereof, configured to receive the distally-extending protrusion of the first housing part, and a second seat adjacent the distal end thereof, configured to rotatably hold a ball applicator.

18 Claims, 7 Drawing Sheets

LIQUID ADHESIVE DISPENSER DEVICE

BACKGROUND OF THE INVENTION

Field of the Invention

The present disclosure relates generally to fluid-dispensing devices and, in particular, to a disposable and/or single-use liquid adhesive dispenser device for dispensing an amount of liquid adhesive to be used for medical procedures, such as intravenous (IV) port securement, insertion site sealing, and/or wound closure procedures.

Description of Related Art

Liquid adhesives, such as curable polymeric solutions, are used for medical procedures, such as to secure an intravenous (IV) port to a patient's skin, as well as for wound closure and insertion site sealing to prevent or reduce microbial ingress. For example, minimally invasive surgery, such as laparoscopic surgery, is typically accomplished using small incisions. Such small incisions can be closed by traditional techniques, such as the introduction of sutures or staples to close the incision wounds. More recently, though, the use of surgical adhesives has gained favor in closing incisions and wounds.

Many different packaging configurations, dispenser devices, and applicators have been developed for providing a predetermined amount of the liquid adhesive to a specific surgical site, such as to a wound or insertion site. For example, liquid adhesives can be provided in disposable pouches or sleeves, which can be punctured or torn to release the liquid adhesive contained therein. Liquid adhesive can also be provided to a patient's skin using disposable tools, such as swabs, brushes, or sponges. More sophisticated dispenser and applicator devices can include sealed ampoules, cartridges, vials, or other containers containing an amount of liquid adhesive to be provided to a wound or incision site. Many existing dispenser devices include a mechanism for opening the container and then allowing the liquid adhesive to drain from the container by gravity. Other dispenser devices can include pumping or squeezing mechanisms for expelling the liquid adhesive from the dispenser device.

However, there is a need for improved dispenser devices that allow a user to precisely control fluid flow rate and volume to deposit a desired amount of the liquid adhesive at a desired surgical/wound site. The dispenser devices of the present disclosure are configured to provide this sort of precise control of fluid release, while also providing long shelf-life and preventing contamination and leakage of the device and/or liquid adhesive contained therein prior to use.

SUMMARY OF THE INVENTION

Provided herein is a liquid adhesive dispenser device, including a housing having a first housing part having a proximal end, a distal end, a first port at the distal end, and a sidewall therebetween defining a first chamber configured to hold a liquid adhesive, a second housing part, having a proximal end, a distal end, a second port at the distal end, and a sidewall therebetween defining a second chamber configured to receive a liquid adhesive, and a ball applicator arranged adjacent the second port, wherein the first housing part has a distally-extending protrusion arranged to seal the first port, wherein the second housing part has a first seat arranged adjacent the proximal end thereof and configured to receive the distally-extending protrusion of the first housing part and a second seat adjacent the distal end thereof and configured to rotatably hold a ball applicator.

In accordance with an embodiment of the present invention, the first port and the protrusion are radially offset from a center of the distal end of the first housing part.

In accordance with an embodiment of the present invention, the first seat is radially offset from a center of the proximal end of the second housing part.

In accordance with an embodiment of the present invention, the first housing part is rotatable relative to the second housing part.

In accordance with an embodiment of the present invention, the protrusion is held within the first seat and is frangible, such that as the first housing part and/or the second housing part are rotated relative to one another, the protrusion is removed from the first port, thereby placing the first chamber in fluid communication with the second chamber.

In accordance with an embodiment of the present invention, the ball applicator is configured to rotate as the device is moved across a patient's skin, thereby allowing for delivery of liquid adhesive to the patient's skin.

In accordance with an embodiment of the present invention, the second port and the ball applicator are arranged such that one or more fluid paths are present between the ball applicator and the sidewalls of the second housing part.

In accordance with an embodiment of the present invention, the second port and the ball applicator are arranged such that one or more slots are present between the ball applicator and the sidewalls of the second housing part.

In accordance with an embodiment of the present invention, the second housing part is collapsible.

In accordance with an embodiment of the present invention, the second housing part comprises one or more grips arranged on an outer surface of the sidewalls.

In accordance with an embodiment of the present invention, the liquid adhesive dispenser device further includes a liquid adhesive received within the first chamber.

In accordance with an embodiment of the present invention, an amount of the liquid adhesive received within the first chamber is a single-use amount.

In accordance with an embodiment of the present invention, the single-use amount is equal to or less than about 1.0 mL, optionally less than about 0.5 mL, optionally less than about 0.2 mL.

In accordance with an embodiment of the present invention, the liquid adhesive includes a tissue adhesive configured to be used for securing a vascular access device to skin of a patient, wound closure, and/or insertion site closure.

In accordance with an embodiment of the present invention, the liquid adhesive includes a cyanoacrylate composition.

In accordance with an embodiment of the present invention, the first housing part includes a flange at the distal end thereof, the flange configured to be received within a recess adjacent the proximal end of the second housing part.

Also provided herein is a kit including a liquid adhesive dispenser device and a package configured to hold the liquid adhesive dispenser device.

In accordance with an embodiment of the present invention, the device is hermetically sealed within the package.

In accordance with an embodiment of the present invention, the device and/or the package are sterilized.

DESCRIPTION OF THE INVENTION

Figure 1:
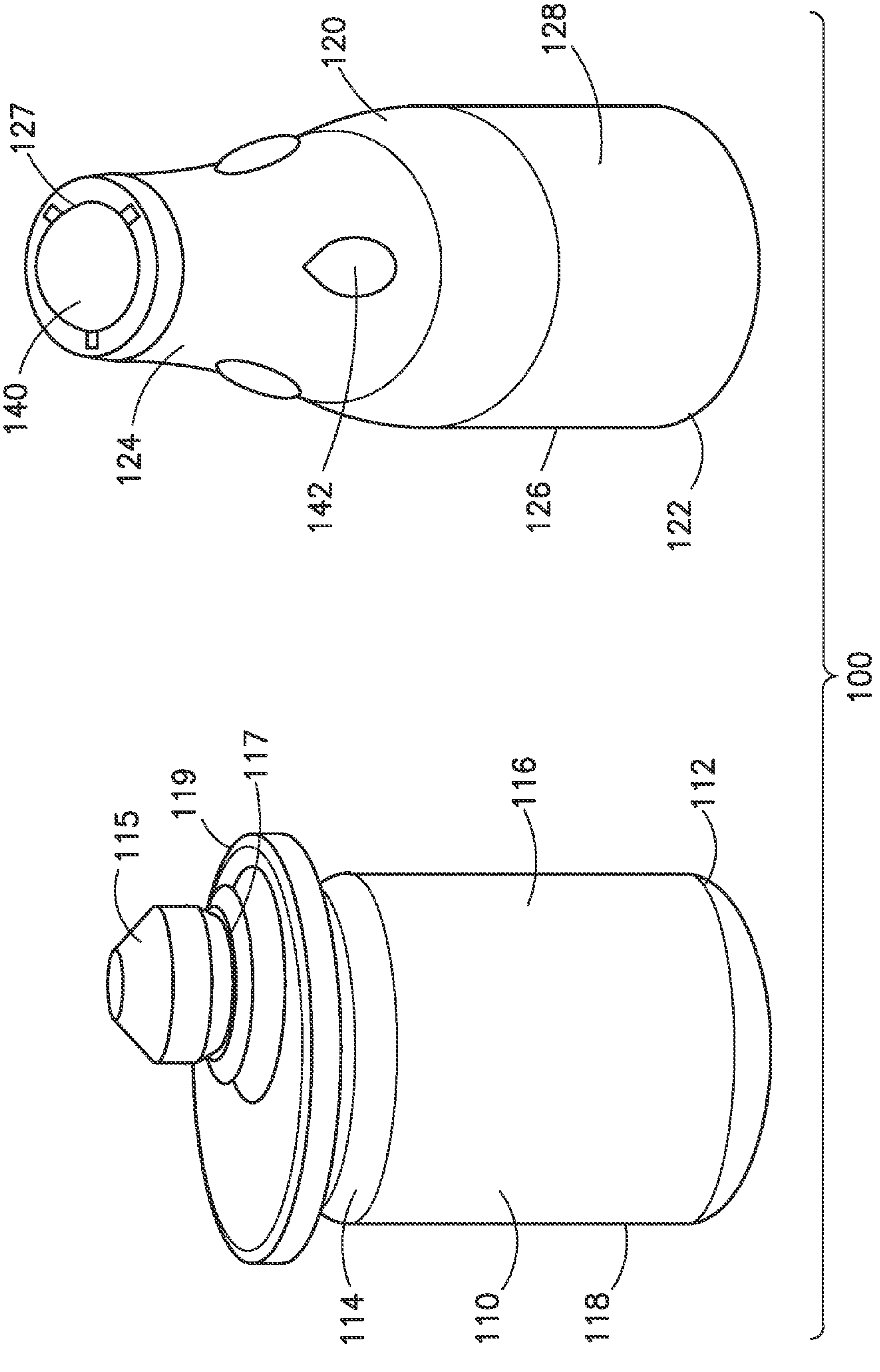
FIG. 1 is a side view of a device according to non-limiting embodiments described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Provided herein is a dispensing device, optionally for a liquid adhesive, which can be used to provide controlled application of a fluid, such as a liquid adhesive, to a site of a skin puncture, for example a venipuncture via a central venous catheter (CVC), a peripheral intravenous catheter (PIVC), or a peripherally-inserted central catheter (PICC).

Figure 2A:
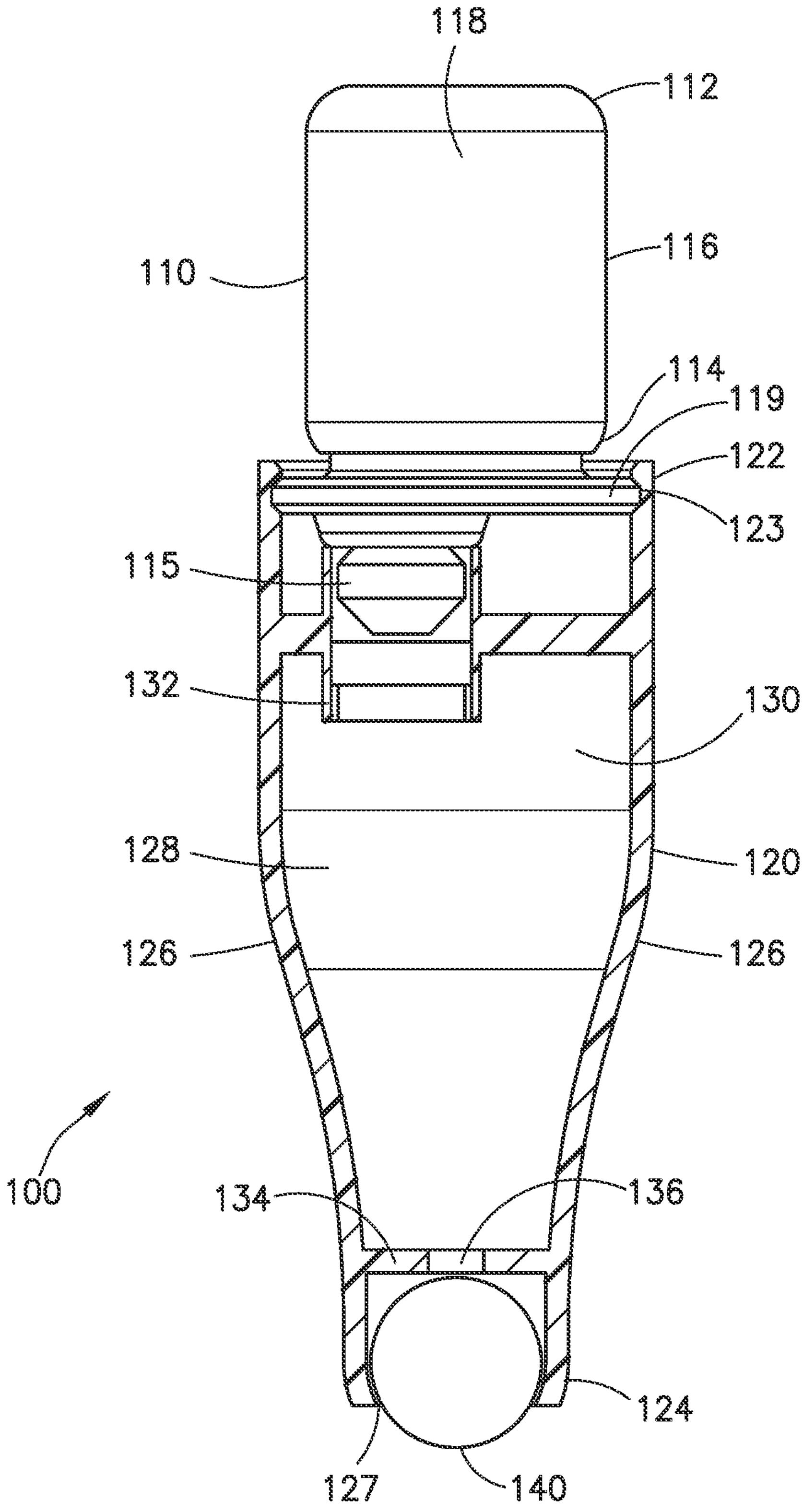
FIG. 2A is a cross-sectional view of a device according to non-limiting embodiments described herein.
Figure 2B:
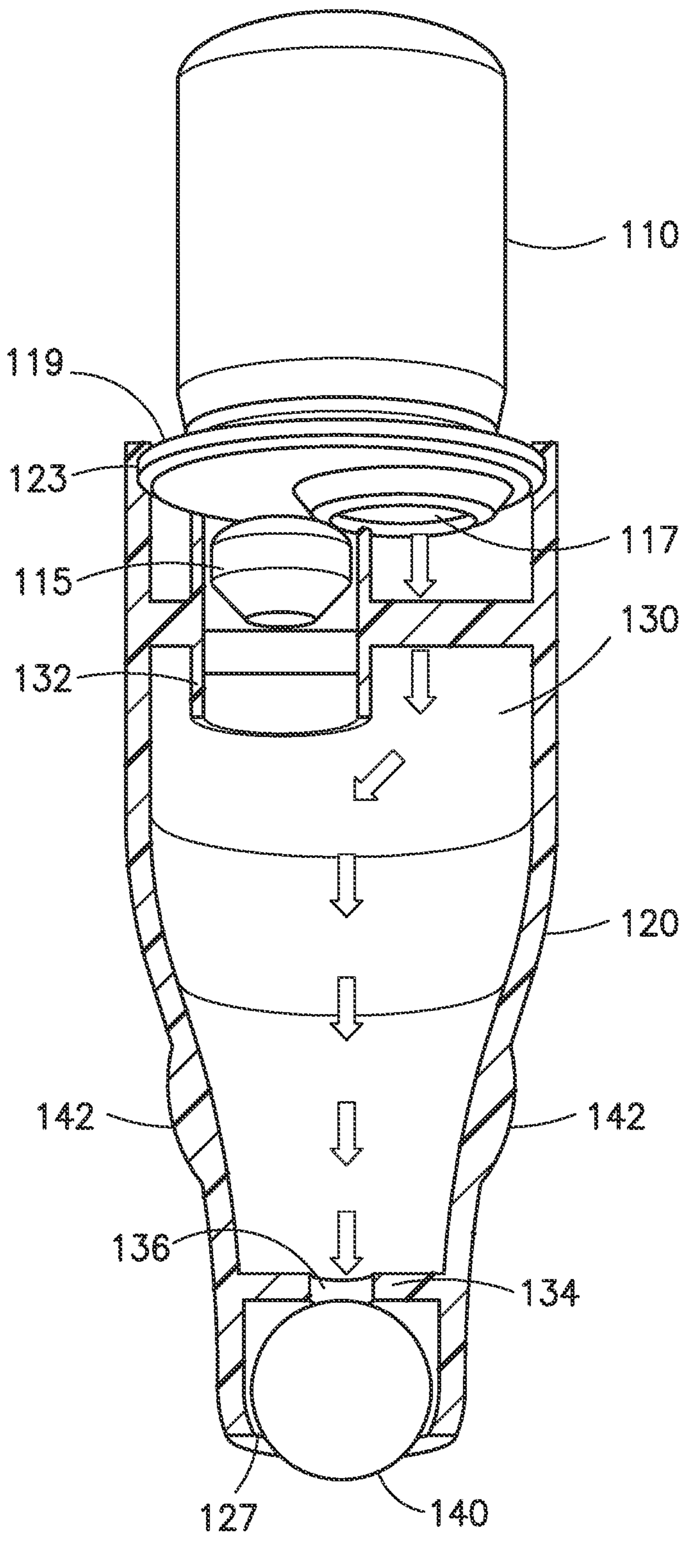
FIG. 2B is a cross-sectional view of a device according to non-limiting embodiments described herein.

Turning to FIG. 1, shown is a non-limiting embodiment of a dispensing device 100, including a first housing part 110 and a second housing part 120. First housing part 110 may be an ampoule, and may include a proximal end 112, a distal end 114, and a sidewall 116 therebetween defining a first chamber 118 configured to receive and/or hold a liquid adhesive. First housing part 110 may be formed of any suitable material, for example a plastic material. In non-limiting embodiments, first housing part 110 is collapsible, such that a user can compress sidewall 116 to expel a liquid adhesive received or held therein. First housing part 110 further may include a first port 117 arranged at distal end 114 thereof, sealed by a protrusion 115. Protrusion 115 may be frangible, and may adopt any suitable shape. As shown in FIGS. 2A-2B, protrusion 115 may be generally circular, and may include a frustoconical portion. Port 117 may be eccentrically arranged at distal end 114 of first housing part 110. For example, port 117 may be radially offset from the center of first housing part 110, for example radially offset from a longitudinal axis extending in a proximal-distal direction through the center of first housing portion 110.

Second housing part 120 may be a nozzle, and may include a proximal end 122, a distal end 124, and a sidewall 126 therebetween defining a second chamber 128 configured to receive and/or hold a liquid adhesive. Second housing part 120 may be formed of any suitable material, for example a plastic material. In non-limiting embodiments, second housing part 120 is collapsible, such that a user can compress sidewalls 126 to expel a liquid adhesive received or held therein. In non-limiting embodiments, sidewall 126 includes one or more grips 142, configured to allow a user to grip sidewall 126 to compress second housing part 120. Second housing part 120 further may include a second port 127 arranged at distal end 124 thereof. Second port 127 may include a ball applicator 140 received within port 127.

Turning to FIGS. 2A-2B, shown is a non-limiting embodiment of dispensing device 100 in its pre-use (FIG. 2A) and use (FIG. 2B) configurations. As shown in these cross-sectional views, ball applicator 140 of second housing part 120 may be secured, optionally in a rotatable manner, within second port 127 by a first seat 134. First seat 134 may be formed of a flange with a passage 136 therethrough to allow for passage of a liquid adhesive through second chamber 128 and out of second port 127. Second housing part 120 further may include a second seat 132, optionally connected to sidewall 126 of second housing part by a flange 130. Second seat 132 may be eccentrically arranged at proximal end 122 of second housing part 120. For example, second seat 132 may be radially offset from the center of second housing part 120, for example radially offset from a longitudinal axis extending in a proximal-distal direction through the center of second housing portion 120.

As shown in FIGS. 2A-2B, first housing part 110 may include a flange 119 at distal end 114 thereof, the flange 119 configured to be received within a corresponding recess 123 in sidewall 126 of second housing part 120, at proximal end 122 thereof. Such an arrangement may allow for a snap fit between first housing part 110 and second housing part 120, while, optionally, maintaining a rotatable relationship between first housing part 110 and second housing part 120. That is, first housing part 110 and second housing part 120 may be secured to one another, and may be rotatable relative to one another.

As shown in FIG. 2A, in a pre-use configuration, protrusion 115, which blocks first port (not shown) of first housing part 110, may be received within seat 132 in second housing part 120. Turning to FIG. 2B, as noted above, first housing part 110 and second housing part 120 may be rotatable relative to one another. Due to the eccentric arrangement of first port 117 (and protrusion 115) and second seat 132, rotation of housing portions 110, 120 relative to one another may cause protrusion 115 to break free from port 117. This breakage places first chamber 118 into fluid communication with second chamber 128, allowing any liquid adhesive received and/or held within first chamber 118 to flow to second chamber 128 (depicted with arrows in FIG. 2B).

As first chamber 118 and second chamber 128 are placed into liquid communication, and liquid adhesive enters second chamber 128, such adhesive can be dispensed through second port 127 in a number of ways. Liquid adhesive may be actively dispensed from device 100 by a user applying pressure to and compressing first housing part 110 and/or second housing part 120. As used herein, "active" dispensing of the liquid adhesive means that some portion or component of the device 100 is operated or actuated to force liquid adhesive from the device 100. In contrast, "passive" dispensing of liquid adhesive refers to movement of fluid by environmental or inherent forces, such as gravity, natural elasticity of components of the container or device, osmosis, differential pressure, etc.

Figure 3A:
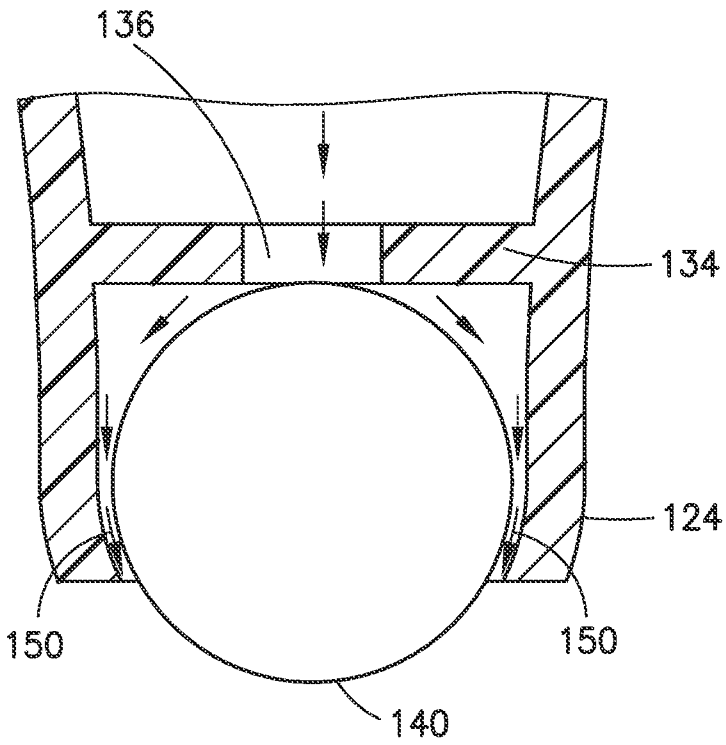
FIG. 3A is a partial cross-sectional view of a device according to non-limiting embodiments described herein.
Figure 3B:
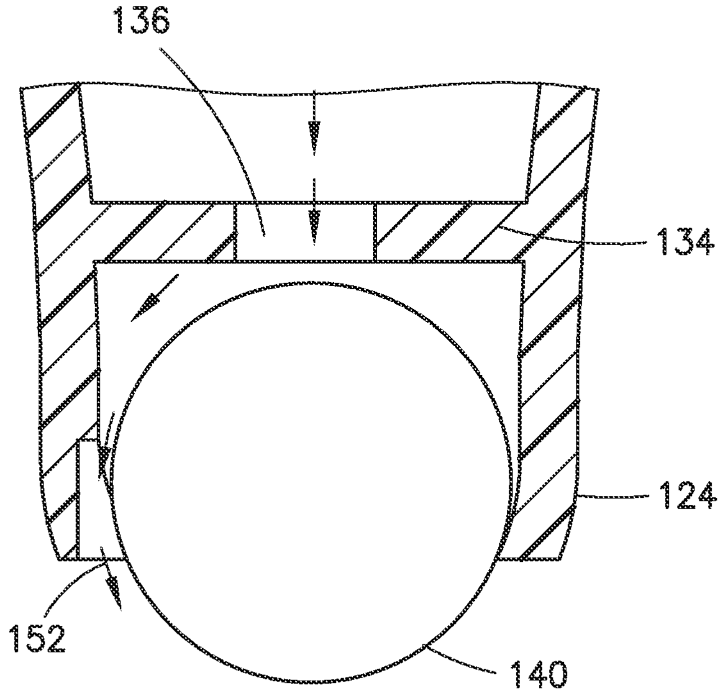
FIG. 3B is a partial cross-sectional view of a device according to non-limiting embodiments described herein.
Figure 4:
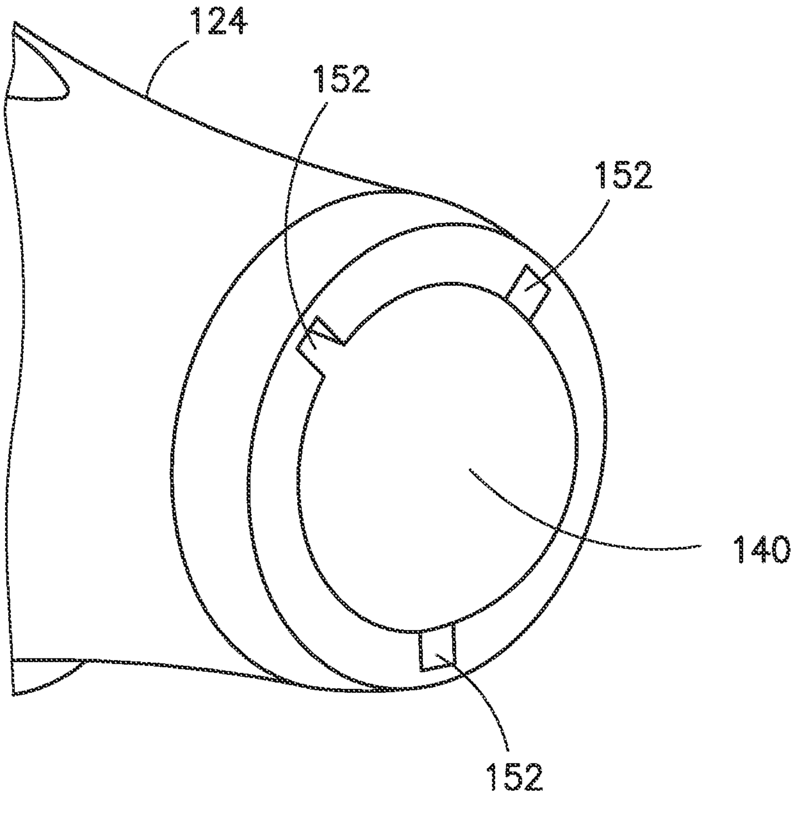
FIG. 4 is a side view of a device according to non-limiting embodiments described herein.

Turning to FIGS. 3A-4, various arrangements of second port 127 and ball applicator 140, optionally for use in passive and/or active dispensing of liquid adhesive, are shown. For example, in the non-limiting embodiment of FIG. 3A, an arrangement where ball applicator 140, first seat 134, and distal end 124 of second housing part 120 is shown where one or more fluid flow channels 150 are arranged about the circumference of ball applicator 140, between ball applicator 140 and distal end 124 of second housing part 120. Liquid adhesive may flow around ball applicator 140, for example by virtue of gravity and/or capillary effect, and may be applied to a region of interest on the patient's skin by rolling the ball applicator 140 thereover. In non-limiting embodiments, distal end 124 of second housing part 120 may include one or more slots 152 therein, as shown, for example, in FIGS. 3B-4. The size and arrangement of slots 152 may be such that liquid adhesive can be dispensed therethrough in the form of droplets, for example through active dispensing as described above. In such embodiments, application of pressure to second housing part 120 may force ball applicator 140 distally, sealing the one or more flow channels 150, forcing liquid adhesive through one or more slots 152 (optionally in droplet form).

Figure 5:
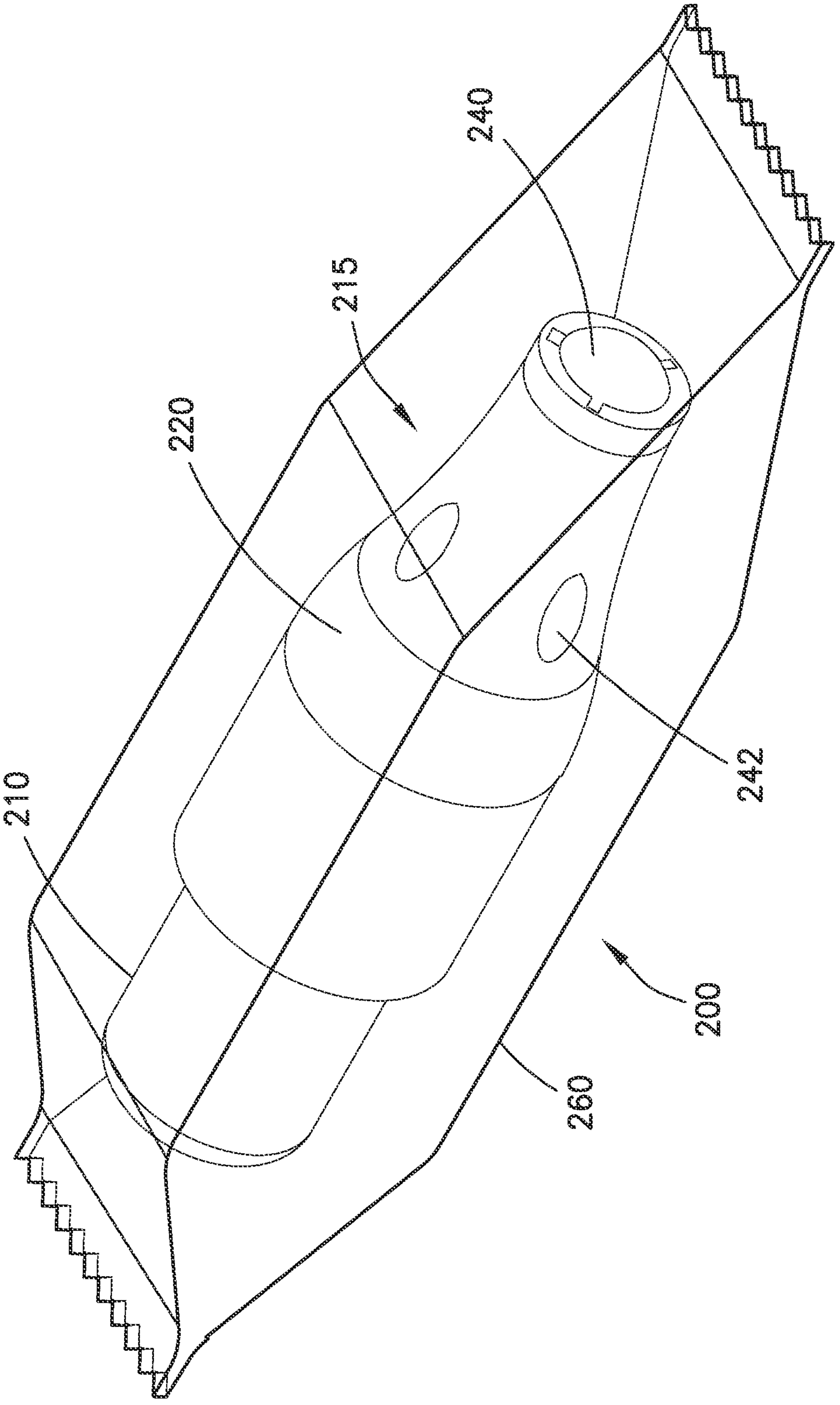
FIG. 5 is a perspective view of a device and packaging therefor according to non-limiting embodiments described herein.

With reference to FIG. 5, also provided herein are kits 200 including a liquid adhesive dispensing device 215 as described herein, and a package 260 in which device 215 may be received. As described previously, device 215 may include a first housing part 210, optionally in the form of an ampoule, a second housing part 220, optionally in the form of a nozzle, a ball applicator 240 arranged at a distal end of second housing part 220, and, optionally, one or more grips 242 arranged on second housing part 220. First housing part 210 and second housing part 220 may include any features described herein. In non-limiting embodiments, device 215 is hermetically sealed within package 260. In non-limiting embodiments, package 260 is tearable, for example at a perforation, to allow for a user to remove device 215 from package 260. In non-limiting embodiments, device 215 and/or package 260 are sterilized when device 215 is packaged, such that device 215 remains sterile inside package 260 in commerce, optionally until device 215 is removed.

With continuing reference to the appended figures, and further to the non-limiting embodiments described above, in non-limiting embodiments, the liquid adhesive is a tissue adhesive, also referred to as surgical glue, skin glue, or liquid stitches, configured to adhere to the skin of a patient. The tissue adhesive can be used, for example, for securing a vascular access device, such as an intravenous (IV) port, to the patient's skin. The tissue adhesive can also be used for wound closure or insertion site sealing to prevent microbial ingress. The dispensing devices 100, 215 disclosed herein may be filled with a variety of different types of biocompatible tissue adhesives, as are known in the art. For example, the tissue adhesive contained in the dispensing devices 100, 215 may be a cyanoacrylate composition.

In some non-limiting embodiments, the dispensing devices 100, 215 disclosed herein may be configured to be single-use and/or disposable devices configured to be disposed of after delivering a single dose or single-use amount of the liquid adhesive. As used herein, a "single-use amount" of the liquid adhesive refers to an amount of adhesive needed for performing common medical actions including, but not limited to, IV port securement, wound closure for small wounds or incisions, and/or insertion site sealing. For example, the dispensing devices 100, 215 may be configured to contain less than about 1.0 mL, preferably less than 0.5 mL, or more preferably less than about 0.2 mL of the liquid adhesive. In other examples, the dispensing devices 100, 215 may contain from about 0.05 mL to about 1.0 mL of the liquid adhesive.

Figure 6:
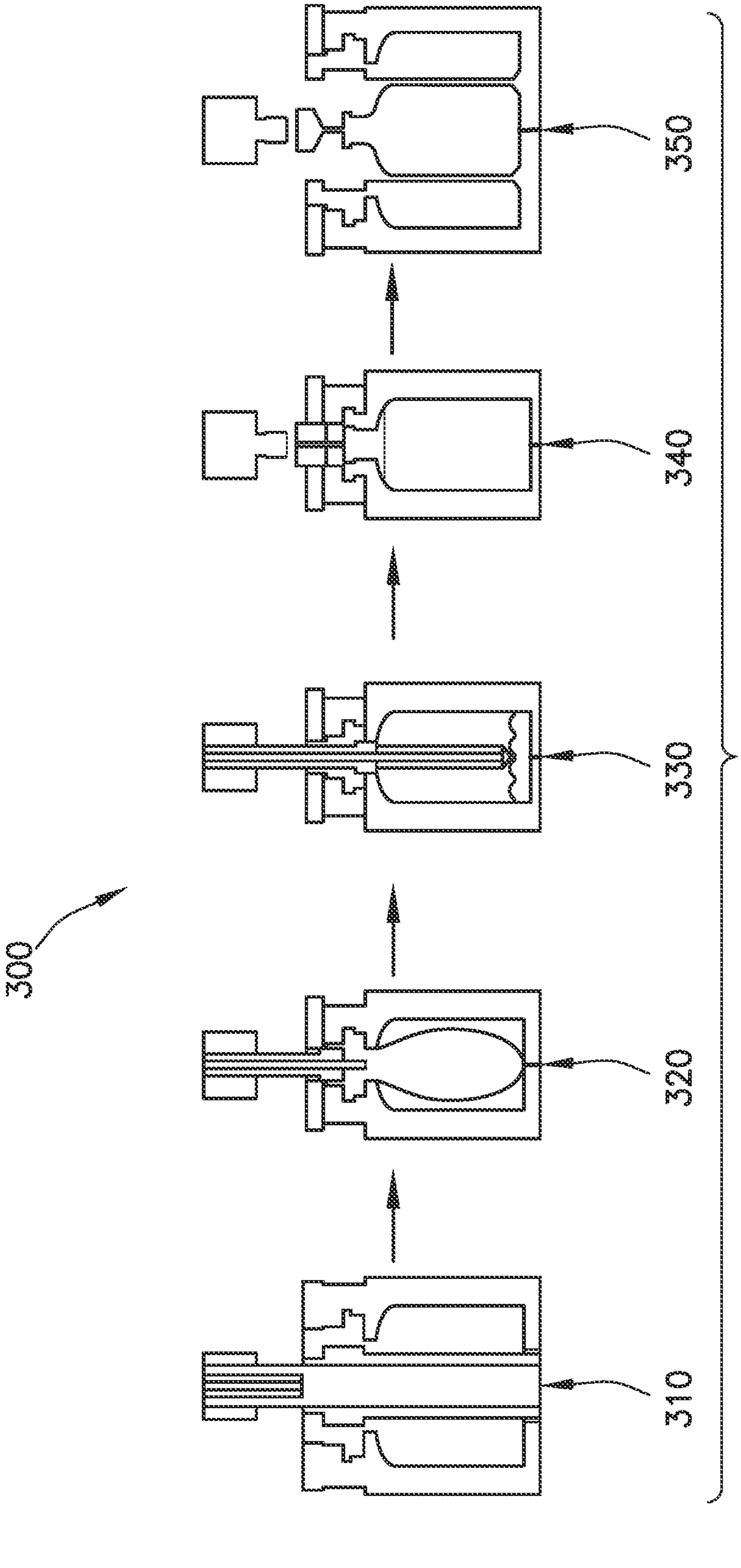
FIG. 6 is a schematic of a process for forming a device according to non-limiting embodiments described herein.

With reference to FIG. 6, also provided herein is a process 300 for manufacturing a liquid adhesive dispensing device as described herein. Process 300 may include a step of extruding 310 a material, for example a polymeric material, into a mold. As described above, any suitable materials may be used, for example materials with resilience, flexibility, and/or elasticity, to allow for the device to be compressed to, when desired, actively dispense liquid adhesive. A step of forming 320 one or more parts of the liquid adhesive dispensing device within the mold may then be performed. In non-limiting embodiments, a first housing part (e.g., an ampoule) is formed in the mold in steps 310 and 320, and is then filled 330 with a liquid adhesive. In such embodiments, a further step of sealing 340 the device, for example an ampoule, may then be performed. Thereafter, the device, for example an ampoule, may be sealed 340 and demolded 350.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A liquid adhesive dispenser device, comprising:

a housing having:

a first housing part comprising a proximal end, a distal end, a first port at the distal end, and a sidewall therebetween defining a first chamber configured to hold a liquid adhesive;

a second housing part comprising a proximal end, a distal end, a second port at the distal end, and a sidewall therebetween defining a second chamber configured to receive a liquid adhesive; and a ball applicator arranged adjacent the second port, wherein the first housing part comprises a distally-extending protrusion arranged to seal the first port, wherein the second housing part comprises a first seat arranged adjacent the proximal end thereof and configured to receive the distally-extending protrusion of the first housing part, and wherein the second housing part comprises a second seat adjacent the distal end thereof and configured to rotatably hold a ball applicator, wherein the first port and the distally extending protrusion are radially offset from a center of the distal end of the first housing part.

2. The device of claim 1, wherein the first seat is radially offset from a center of the proximal end of the second housing part.

3. The device of claim 2, wherein the first housing part is rotatable relative to the second housing part.

4. The device of claim 3, wherein the protrusion is held within the first seat and is frangible, such that as the first housing part and/or the second housing part are rotated relative to one another, the protrusion is removed from the first port, thereby placing the first chamber in fluid communication with the second chamber.

5. The device of claim 4, wherein the ball applicator is configured to rotate as the device is moved across a patient's skin, thereby allowing for delivery of liquid adhesive to the patient's skin.

6. The device of claim 1, wherein the second port and the ball applicator are arranged such that one or more fluid paths are present between the ball applicator and the sidewall of the second housing part.

7. The device claim 1, wherein the second port and the ball applicator are arranged such that one or more slots are present between the ball applicator and the sidewall of the second housing part.

8. The device of claim 1, wherein the second housing part is collapsible.

9. The device of claim 1, wherein the second housing part comprises one or more grips arranged on an outer surface of the sidewall.

10. The device of claim 1, further comprising a liquid adhesive received within the first chamber.

11. The device of claim 10, wherein an amount of the liquid adhesive received within the first chamber is a single-use amount.

12. The device of claim 11, wherein the single-use amount is equal to or less than about 1.0 mL.

13. The device of claim 1, wherein the liquid adhesive comprises a tissue adhesive configured to be used for securing a vascular access device to skin of a patient, wound closure, and/or insertion site closure.

14. The device of claim 1, wherein the liquid adhesive comprises a cyanoacrylate composition.

15. The device of claim 1, wherein the first housing part comprises a flange at the distal end thereof, the flange configured to be received within a recess adjacent the proximal end of the second housing part.

16. A kit comprising:

a liquid adhesive dispenser device, comprising:

a housing having:

a first housing part comprising a proximal end, a distal end, a first port at the distal end, and a sidewall therebetween defining a first chamber configured to hold a liquid adhesive;

a second housing part comprising a proximal end, a distal end, a second port at the distal end, and a sidewall therebetween defining a second chamber configured to receive a liquid adhesive; and a ball applicator arranged adjacent the second port, wherein the first housing part comprises a distally-extending protrusion arranged to seal the first port, wherein the second housing part comprises a first seat arranged adjacent the proximal end thereof and configured to receive the distally-extending protrusion of the first housing part, and wherein the second housing part comprises a second seat adjacent the distal end thereof and configured to rotatably hold a ball applicator, wherein the first port and the protrusion are radially offset from a center of the distal end of the first housing part; and a package configured to receive the device therein.

17. The kit of claim 16, wherein the device is hermetically sealed within the package.

18. The kit of claim 16, wherein the device and/or the package are sterilized.

* * * * *